US007011958B2

(12) United States Patent
Watzele et al.

(10) Patent No.: US 7,011,958 B2
(45) Date of Patent: Mar. 14, 2006

(54) METHOD FOR IMPROVING THE STABILITY OF LINEAR DNA IN CELL-FREE IN VITRO TRANSCRIPTION/TRANSLATION SYSTEMS

(75) Inventors: Manfred Watzele, Weilheim (DE); Thomas Hoffmann, Neu-Edingen (DE); Cordula Nemetz, Wolfratshausen (DE); Dieter Heindl, Tutzing (DE); Thomas Metzler, Munich (DE); Wolfgang Mutter, Bernried (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 156 days.

(21) Appl. No.: 10/124,663

(22) Filed: Apr. 17, 2002

(65) Prior Publication Data

US 2003/0073201 A1 Apr. 17, 2003

(30) Foreign Application Priority Data

Apr. 18, 2001 (DE) ............................. 101 19 006

(51) Int. Cl.
C12P 21/06 (2006.01)
C12P 19/34 (2006.01)
(52) U.S. Cl. ..................... 435/68.1; 435/69.1; 435/91.2
(58) Field of Classification Search ............... 435/91.2, 435/69.1, 6, 68.1
See application file for complete search history.

(56) References Cited

U.S. PATENT DOCUMENTS

| | | | | |
|---|---|---|---|---|
| 5,571,690 | A | 11/1996 | Hecht | 435/69.1 |
| 6,027,913 | A | 2/2000 | Sommer | 435/69.1 |
| 6,323,009 | B1 * | 11/2001 | Lasken et al. | 435/91.1 |
| 2003/0082559 | A1 * | 5/2003 | Beach et al. | 435/6 |

FOREIGN PATENT DOCUMENTS

| | | |
|---|---|---|
| EP | 0416817 B1 | 3/1991 |
| EP | 0967274 A2 | 12/1999 |
| JP | 11-323141 | 5/2001 |

OTHER PUBLICATIONS

Gibco Catalog 1994-1995, 12-16.*
Martemyanov et al. Direct expression of PCR products in a cell-free transcription/translation system: synthesis of antibacterial peptide cecropin FEBS Letters vol. 414 1997.*
Hirao et al. Stabilization of mRNA in an *Escherichia coli*-free translation system vol. 321 No. 2,3 pp 169-172.*
Gibco Catalog 1994-1995, 12-16.*
Bassett, Carole Leavel, et al., "In Vitro Coupled Transcription-Translation of Linear DNA Fragments in a Lysate Derived from a recB rna pnp Strain of *Escherichia coli*," Journal of Bacteriology, vol. 156, No. 3, Dec. 1983, p. 1359-1362.

Hirao, Ichiro, et al., "Stabilization of mRNA in an *Escherichia coli* cell-free translation system," FEBS 12376, vol. 321, No. 2,3, 169-172, Apr. 1993.
Kain, Kevin C., et al., "Universal Promoter for Gene Expression Without Cloning: Expression-PCR," Research Report, Department of Immunology, Walter Reed Army Institute of Research, Washington, D.C. 20307-5100, 6pages.
Kandimalla, Ekambar R., et al., "Mixed backbone antisense oligonucleotides: design, biochemical and biological propertieof oligonucleotides containing 2'-5'-ribo- and 3'-5'-deoxyribonucleotide segments," Nucleic Acids Research, 1997, vol. 25,No. 2, 370-378, 1997 Oxford University Press.
Lesley, Scott A., et al., "Use of in Vitro Protein Synthesis from Polymerase Chain Reaction-generated Templates to Study Interaction of *Escherichia coli* Transcription Factors with Core RNA Polymerase and for Epitope Mapping of Monoclonal Antibodies," The Journal of Biological Chemistry, vol. 266, No. 4, Issue of Feb. 4, pp. 2632-2638, 1991.
Martemyanov, Kirill A., et al., "Direct expression of PCR products in a cell-free transcription/translation system: synthesis of antibacterial peptide cecropin," FEBS Letters 414 (1997) pp. 268-270.
Nakano, Hideo, et al., "Efficient Coupled Transcription/Translation from PCR Template by a Hollow-Fiber Membrane Bioreactor," Biotechnology and Bioengineering, vol. 64, No. 2, Jul. 20, 1999, pp194-199.
Pandolfi, Daniela, et al., "Evaluation of Different Types of End-Capping Modifications on the Stability of Oligonucleotides Toward 3'- and 5' - Exonucleases," Nucleosides & Nucleotides, 18(9), 2051-2069 (1999).
Tang, Jin yan, et al., "Self-stabilized antisense oligodeoxynucleotide phosphorothioates: properties and anti-HIV activity," Nucleic Acids Research, 1993, vol. 21, No. 11, 2729-2735
Tohda, Hideki, et al., "Efficient expression of *E. coli* dihydrofolate reductase gene by an in vitro translation system using phosphorothioate mRNA," Journal of Biotechnology 34(1994) 61-69.

(Continued)

Primary Examiner—James Ketter
Assistant Examiner—Konstantina Katcheves
(74) Attorney, Agent, or Firm—Roche Diagnostics Operations, Inc.; Marilyn L. Amick (57) ABSTRACT

The present invention concerns a method for improving the stability of linear short DNA towards exonucleases in cell-free in vitro transcription/translation systems using lysates containing exonucleases or in cellular systems containing exonucleases, wherein the stability of the linear short DNA is improved by adding unspecific linear DNA.

6 Claims, 4 Drawing Sheets

OTHER PUBLICATIONS

Verheijen, Jeroen C., et al., "Incorporation of a 4-Hydroxy-N-acetylprolinol Nucleotide Analogue Improves the 3'-Exonuclease Stability of 2'-5'-Oligoadenylate-Antisense Conjugates," Bioorganic & Medicinal Chemistry Letters 10 (2000) 801-804.

Yang, Huey-Lang, et al., "Cell-free coupled transcription-translation system for investigation of linear DNA segments," Proc, Natl. Acad. Sci. USA, vol. 77, No. 12, pp 7029-7033, Dec. 1980, Biochemistry.

Yang, Junhao, et al., "In Vitro Analysis of Roles of a Disulfide Bridge and a Calcium Binding Site in Activation of *Pseudomonas* sp. Strain KWI-56 Lipase," Journal of Bacteriology, vol. 182, No. 2, Jan 2000, pp. 295-302.

Yoshizawa, Satoko, et al., "Nuclease resistance of an extraordinarily thermostable mini-hairpin DNA fragment, d(GCGAAGC) and its application to in vitro protein synthesis," Nucleic Acids Research, 1994, vol. 22, No. 12, pp. 2217-2221 1994 Oxford University Press.

* cited by examiner

SEQUENCE LISTING

```
<160> NUMBER OF SEQ ID NOS: 3

<210> SEQ ID NO 1
<211> LENGTH: 7
<212> TYPE: DNA
<213> ORGANISM: Artificial Sequence
<220> FEATURE:
<223> OTHER INFORMATION: This is a generic sequence found in hairpin
      loops

<400> SEQUENCE: 1 gcgaagc                                                                 7

<210> SEQ ID NO 2
<211> LENGTH: 66
<212> TYPE: DNA
<213> ORGANISM: Artificial Sequence
<220> FEATURE:
<223> OTHER INFORMATION: sense primer

<400> SEQUENCE: 2
gcttagatcg agatctcgat cccgcgaaat taatacgact cactataggg agaccacaac      60
ggtttc                                                                 66

<210> SEQ ID NO 3
<211> LENGTH: 49
<212> TYPE: DNA
<213> ORGANISM: Artificial Sequence
<220> FEATURE:
<223> OTHER INFORMATION: antisense primer

<400> SEQUENCE: 3
ggaagctttc agcaaaaaac ccctcaagac ccgtttagag gccccaagg                  49
```

METHOD FOR IMPROVING THE STABILITY OF LINEAR DNA IN CELL-FREE IN VITRO TRANSCRIPTION/TRANSLATION SYSTEMS

The present invention concerns a method for improving the stability of linear short DNA from degradation by exonucleases in cell-free in vitro transcription/translation systems using lysates containing exonucleases or in cellular systems, wherein the stability of the linear short DNA is improved by adding unspecific linear DNA.

Cell-free DNA-dependent in vitro transcription/translation works quite well in practice with respect to the expression of circular double helix DNA and with respect to the expression of long linear DNA. Attempts at expressing shorter linear DNA pieces had only limited success. The smaller the DNA that is used the more difficult it was to obtain appreciable amounts of gene product. It was established that these difficulties were due to the presence of exonucleases. Hence it was shown that exonuclease V is responsible for the degradation of linear DNA when S30 lysates of E. coli were transcribed and translated in vitro. Exonuclease V is composed of three subunits (the gene products recB, recC, redD). This exonuclease cleaves the linear DNA starting at its 3' end.

It was attempted to remedy this problem by mutating the subunits of this exonuclease in order to remove the lytic activity. Yang et al., (1980) PNAS vol. 77, No. 12, pp 7029–7033 describe an improved protein synthesis starting from linear DNA templates using the E. coli strain CF300 after deletion of exonuclease V (elimination of the genes recB, recC; strain recB21).

Leavel Basset et al., 1983 additionally mutated the RNase and polynucleotide phosphorylase genes (rna-19 pnp-7) in the recB21 strain (strain CLB7) and achieved a significantly higher protein expression with linear DNA templates after a one hour incubation period. Lesley et al., 1991 use an exonuclease V-deficient recD BL21 strain which was referred to as the SL119 strain and describe for the first time the method of in vitro protein synthesis starting from PCR-generated templates. Lysates of the strain SL119 are commercially available (Promega) for in vitro transcription/translation using linear templates.

However, a disadvantage of the measures described above is that all these mutants grow more slowly and also the lysates obtained from these strains have a significantly poorer rate of synthesis. Apparently this exonuclease plays an important role in the metabolism of the bacteria. Hence it appears to be important to use lysates or cell cultures in which exonucleases are present.

Another conceivable measure to nevertheless protect the nucleic acids against exonucleolytic degradation is to modify the nucleic acids either by protecting both ends or by using modified nucleotide building blocks as described in the literature for nucleic acids in the anti-sense field and in the following citations.

Single-stranded DNA/RNA molecules can be protected by protecting the ends with alkyl groups and by modifying the bases; Pandolfi et al., (1999) Nucleosides & Nucleotides. 18(9), 2051–2069. Verheijen et al. (2000) Bioorganic & Medicinal Chemistry Letters 10, 801–804 show an increased stability of single-stranded DNA molecules by protecting the ends with 4-hydroxy-N-acetylprolinol, L-serinol or by 3'-3'-phosphodiester bonds. Pure or mixed phosphorothioate bonds and chemically modified oligonucleotides e.g. methylphosphonates and phosphoramidates are more stable and are degraded more slowly by exonucleases Kandimalla et al., NAR (1997) vol. 25. No. 2, pp 370–378. Tohda et al., (1994) Journal of Biotechnology 34 (1994) 61–69 show that RNA containing phosphorothioates is more stable towards nucleases and therefore has a higher translation efficiency. However, on the whole only small amounts of protein could be produced. Tang et al., (1993) NAR, vol. 21, No. 11, pp 2279–2735 show that hairpin loop structures protect the 3' end of single-stranded DNAs against exonucleolytic degradation. Hirao et al., (1993) FEBS, vol. 321, No. 2, 3, 169–172 show that the hairpin, which the DNA fragment d(GCGAAGC) forms, is extremely resistant to nucleases from E. coli extracts. Yoshizawa et al., (1994) NAR, Vol. 22, No. 12, pp 2217–2221 describe that a stabilization of the 3' end of mRNA by hybridization with the same hairpin results in a 200-fold increase in the efficiency of in vitro translation with E. coli extracts. Good and Nielsen (1998) PNAS USA 95, 2073–6 show that synthetic molecules containing bases that are coupled to a peptide backbone (peptide nucleic acid, PNA) are resistant to hydrolytic cleavage in E. coli extracts and can be used as anti-sense molecules. Burdick and Emlen (1985) J. Immunology 135, 2593–7 describe that in DNA anti-DNA immunocomplexes, IgG molecules can protect the DNA that is bound to them from nucleolytic degradation. EP 0 967 274 A2 describes methods for preparing dumbbell-shaped linear double-stranded DNA molecules. In this method a plasmid is cleaved with restriction enzymes and the resulting double-stranded non-covalently closed molecules are then modified to form dumbbell-shaped constructs by digesting the ends with a restriction endonuclease that forms single-stranded overhangs and subsequently ligating matching hairpin oligomers onto the resulting single-strand overhangs. This construct has an increased stability towards the exonucleases of T7 DNA polymerase.

A disadvantage of these measures is that the synthesis of these modified nucleotide building blocks is often very complicated. On the one hand, the preparation of modified nucleotides is complicated and expensive. On the other hand, additional time-consuming process steps are required to incorporate the modification. In addition difficulties can arise in using the modified nucleic acids as templates. In the case of phosphothioates a disadvantage is for example that the synthesis is very complicated and a mixture of diastereomers is formed which, after incorporation, is not optimally suitable as a template for transcription or translation.

Other cell-free expression systems without protection strategies are described in the prior art.: In U.S. Pat. No. 5,571,690 Hecht describes a method for the cell-free synthesis of a protein starting with a template which was generated in a PCR reaction. In this method he amplifies the entire gene sequence including the phage promoter region from a plasmid. After an in vitro transcription he uses a lysate from rabbit reticulocytes for the translation. With this method it was possible to produce 57 µg/ml of a protein using mRNA which was modified after transcription with a 5'CAP. Martemyanov et al., (1997) FEBS Lett. 414, 268–270 use an S30 extract from E. coli for the cell-free synthesis of a protein starting with a template which was generated in a 2-step PCR reaction. In this method the target gene is firstly amplified in a PCR reaction with the aid of two gene-specific oligonucleotide primers and subsequently subjected to a second PCR reaction in which a so-called megaprimer is used to fuse the T7 promoter and the ribosomal binding site to the amplified gene. It was only possible to produce radioactively detectable amounts of protein. Yang et al., (2000) J. Bacteriol. 182, 295–302 use an S30 extract from E. coli to demonstrate the cell-free synthesis of a protein starting with a template which was generated in a PCR reaction. It was only possible in this method to produce radioactively detectable amounts of protein. Nakano et al., (1999) Biotechnol. & Bioeng. 64, 194–199 use an S30 extract from *E. coli* in a hollow fibre reactor to at least produce 80 μg/ml protein reaction mixture starting with a template which was generated in a PCR reaction. In U.S. Pat. No. 6,027,913 Sommer used an extract from reticulocytes for the cell-free synthesis of a protein starting with a template which was generated in a single step PCR reaction. In this method the T7 promoter and the ribosomal binding site are fused to the target gene. Even with this method only small amounts of protein were produced.

However, the methods described above are not satisfactory. Although eukaryotic lysates from rabbit reticulocytes are relatively nuclease-free, a disadvantage is that these lysates cannot be produced economically in large amounts. They only allow very small protein yields. The same applies to lysates from wheat germs which either have to be very laboriously prepared or they are otherwise strongly contaminated with translation-inhibiting factors from the surrounding tissue (JP 236 896).

In contrast *E. coli* lysates yield much larger amounts of protein. However, the described methods for preparing lysates from *E. coli* only allow relatively short reaction periods of up to about one hour with linear DNA templates since afterwards these DNA templates are completely degraded by the exonucleases contained in the lysate. The lysates obtained from *E. coli* exonuclease mutants (i.e. exonuclease-deficient strains) have a significantly poorer synthesis performance than comparable wildtype strains such as the A19 strain for example.

The methods for protecting mRNA have the disadvantage that firstly an in vitro transcription has to be carried out before the protected mRNA can be added to the lysate. This in turn does not permit a coupled reaction and a continuous RNA synthesis. Methods for protecting RNA are described in Tohda et al. (1994) Journal of Biotechnology 34 (1994) 61–69, Yoshizawa et al., (1994) NAR, vol. 22, pp 2217–2221.

Hence the object of the present invention was a method for improving the stability of linear short DNA towards exonucleases in cell-free DNA-dependent in vitro transcription/translation systems using lysates containing exonucleases or in cellular systems.

This object was achieved according to the invention by a method for improving the stability of linear short DNA towards exonucleases in cell-free DNA-dependent in vitro transcription/translation systems using lysates containing exonucleases or in cellular systems wherein the stability of the linear short DNA is improved by adding unspecific linear DNA.

The method according to the invention is preferably used for coupled in vitro transcription/translation systems. Coupled in the sense of the present invention means that the transcription and translation occur concurrently in one reaction. Coupled in the sense of the present invention can also mean that the mRNA molecules which have just been formed by transcription are already translated by the ribosomes.

The method according to the invention is particularly preferably used for cell-free in vitro transcription/translation systems using lysates containing exonucleases. The method is especially used for cell-free in vitro transcription/translation systems using lysates containing exonucleases from prokaryotes e.g. lysates from *E. coli*.

The present invention also concerns the use of the method according to the invention for cell-free in vitro transcription/translation systems using eukaryotic lysates containing exonucleases. These lysates can be from oocytes or eggs e.g. from Xenopus. It is also possible to use lysates from wheat germs or rabbit reticulocytes. The method according to the invention can also be used when the lysates containing exonuclease are lysates from eukaryotic cells which have been grown in cell culture.

The use of a prokaryotic lysate is most preferred according to the invention. Although the common eukaryotic lysate from rabbit reticulocytes contains a much smaller quantity of exonucleases than that of the prokaryote *E. coli* for example and would therefore be preferred with regard to the stability of linear templates. However, the use of a prokaryotic lysate is nevertheless advantageous since, in contrast to eukaryotic ribosomes, the prokaryotic ribosomes do not need a CAP structure for a high synthesis rate. This CAP structure cannot in turn be formed in a coupled transcription/translation reaction i.e. a reaction with concurrent transcription and translation.

Short DNA in the sense of the present invention means that only up to 10,000 additional phase pairs are present before and after a gene (i.e. gene including its regulatory elements such as promoter, terminator, translation-increasing elements).

However, the added linear DNA (sacrificial or competitor DNA) should not result in an undesired background synthesis of proteins. Hence the added DNA must be unspecific. Within the sense of the present invention unspecific DNA means that the added linear DNA is not transcribed in the existing in vitro transcription/translation system.

Various measures can be used to ensure that the added linear DNA is not transcribed. In in vitro transcription/translation systems using exonuclease-containing lysates, RNA polymerases are preferably used which only bind the DNA to be expressed or can only use the DNA to be expressed as a template for RNA synthesis but not the added unspecific DNA. This is further illustrated by the following case:

It is intended to transcribe prokaryotic DNA. In this case it is possible to use a prokaryotic RNA polymerase or an RNA polymerase from bacteriophages such as that of the T7, T3 or SP6 phages as the polymerase which recognizes the corresponding prokaryotic T7, T3 or SP6 promoter but not the promoters of eukaryotic systems. Hence in this case eukaryotic DNA can be added as the unspecific DNA. Thus only the gene after a prokaryotic T7, T3 or SP6 promoter will be transcribed but not the added eukaryotic DNA which is therefore referred to as unspecific for the system that is used (gene with prokaryotic, T7, T3 or SP6 promoter plus prokaryotic T7, T3 or SP6 promoter).

In cases where the sacrificial DNA is eukaryotic DNA it is preferable to add sheared DNA from herring sperm, salmon sperm or calf thymus.

Thus one method from preventing the expression of the sacrificial DNA is for the added DNA to be from a foreign species or to contain no regulatory elements that could be recognized by the polymerase used for the expression.

Another preferred measure for preventing unspecific expression for the method according to the invention in in vitro transcription/translation systems using exonuclease-containing lysates is to inhibit the polymerases that may be present in the lysates or cellular systems in order to prevent unspecific expression of added DNA or of DNA present in the lysates/cellular systems.

It is particularly preferred when the transcription of unspecific DNA is prevented by inhibiting DNA-dependent RNA polymerases which would also transcribe unspecific DNA. Hence if for example the in vitro translation system is an in vitro transcription/translation system using exonuclease-containing lysates that are obtained from prokaryotes such as *E. coli* lysates, the gene to be expressed can be provided with a promoter, as described above, which is only recognized by a bacteriophage RNA polymerase such as T7, T3 or SP6 RNA polymerase. Then the T7, T3 or SP6 RNA polymerase is added, (first measure for preventing unspecific expression). A substance such as rifampicin is added as an additional measure which inhibits DNA-dependent RNA polymerases in the prokaryote lysate. Hence only the bacteriophage RNA polymerase such as T7, T3 or SP6 RNA polymerase is active, which only recognizes the promoter of the gene to be expressed. These measures largely suppress unspecific expression.

An additional or alternative measure is to add other substances instead of rifampicin such as streptolydigin, tirandamycin, sorangicin or rifamycin derivatives which inhibit chain extension of RNA by binding to the DNA-dependent RNA polymerases of the prokaryote lysates.

In the case of in vitro transcription/translation systems using exonuclease-containing lysates that are derived from eukaryotes, a substance can be added to prevent unspecific expression which inhibits RNA polymerase II in the eukaryotic lysates e.g. alpha-amanitin. Then special polymerases can be added such as T7, T3 RNA polymerase or SP6 RNA polymerase which only accept the gene to be expressed as a template when the gene is located behind an appropriate promoter.

According to the inventive method it is preferable to add unspecific DNA at a concentration of 1 to 200 µg/ml per translation mixture. A concentration of 10 to 100 µg/ml per translation mixture is particularly preferred.

Furthermore it is preferred that the unspecific DNA has a length of at least 10 bp.

An advantage of the method according to the invention is that genes do not have to be cloned in a complicated manner into a circular plasmid vector in order to enable protein synthesis, but that the desired gene can be amplified directly from a gene bank or RNA fraction by PCR or RT-PCR for a protein expression. The promoter and terminator regions required for expression can additionally be inserted in this PCR.

It is also conceivable that such unspecific DNA is added in so-called DNA immunization with a linear DNA expression construct. In DNA immunization it is usual to inject a DNA expression construct into the animal which is then taken up and expressed by the cells of the animals. Until uptake into the cells the DNA piece is exposed to exonucleolytic attack and the added unspecific DNA would protect against this.

The advantages of the DNA stabilization according to the inventive method are that the template can continuously reform mRNA and hence the process of protein synthesis can proceed for a longer period in for example the CFCF and CECF processes described by Spirin et al., EP 0 312 617, EP 0 401 369. In the CFCF and CECF techniques cited by Spirin the in vitro translation/transcription is supplied with new substrates and reaction products are continuously removed. The in vitro transcription/translation reaction can thus proceed over a longer period i.e. up to several days. Hence the DNA template has to be protected for a longer period than would be the case in a usual in vitro translation/transcription which lasts for 30 minutes up to a maximum of two hours.

It was shown that the expression of a protein starting with a linear template could be increased several-fold by the method according to the invention.

The present invention also concerns a kit consisting of one or several vessels which contain the following components:
a lysate containing ribosomes prepared from prokaryotic or eukaryotic cells by methods which are known to a person skilled in the art for producing lysates for in vitro translation;
one or more of the 20 naturally-occurring L-amino acids;
one or more naturally-occurring or synthetic t-RNAs
one or more naturally-occurring nucleotides which can be unphosphorylated or be present as monophosphates, diphosphates or triphosphates;
linear unspecific DNA.

The present invention also concerns a reagent solution containing
a lysate containing ribosomes prepared from prokaryotic or eukaryotic cells by methods which are known to a person skilled in the art for producing lysates for in vitro translation;
one or more of the 20 naturally-occurring L-amino acids;
one or more naturally-occurring or synthetic t-RNAs
one or more naturally-occurring nucleotides which can be unphosphorylated or be present as monophosphates, diphosphates or triphosphates;
linear unspecific DNA.

Methods which are known to a person skilled in the art for producing lysates for in vitro translation are described for example in Zubay, G (1973) Annu. Rev. Genet. 7, 267 ("Prokaryotische Extrakte"); Clemens M. J. & Pruijn G. J. M. (1999) pp 129–168 in Protein Expression—A practical Approach, Higgins, S. J. & Hames, B. D. eds. Oxford University Press.

FIGURE LEGENDS

lanes 8–13: in vitro transcription/translation mixtures with addition of 520 µg/ml sheared herring sperm DNA in each case after 0, 2, 5, 30, 60 and 120 min incubation period.

lane 14: plasmid fragments having a size of 2830 and 1321 base pairs before incubation.

Blue columns: transcription/translation mixtures of the green fluorescent protein (GFP) gene starting with linear DNA (EcoRV/Sph1-cleaved pIVEX2.1 GFP plasmid) incubated with a lysate from *E. coli*. 0, 1, 2, and 5 µg unspecific, sheared herring sperm DNA was added to the mixtures.

Red columns: Mixtures containing uncleaved circular pIVEX2.1 GFP plasmid to which 0, 1, 2 and 5 µg unspecific, sheared herring sperm DNA was added.

Red curve: addition of 0 to 7 μg unspecific sheared herring sperm DNA to transcription/translation mixtures of the green fluorescent protein gene starting with a linear template DNA incubated with a lysate from *E. coli*. 0, 1, 2 and 5 μg unspecific sheared herring DNA was added to the mixtures.

Blue curve: addition of 0 to 7 μg circular pBR322 plasmid (instead of sheared herring sperm DNA) to the transcription/translation mixtures.

Hence it can be seen already with an unpurified PCR product that protein synthesis is possible in a coupled transcription/translation mixture containing an *E. coli* S30 lysate when linear unspecific DNA is added.

Column 1 and 2 unpurified PCR product containing a coding sequence for GFP and the control elements T7 promoter, ribosomal binding site and T7 terminator.

Columns 3 and 4 purified PCR product. Column 5 positive control: EcoRV/Sph1-cleaved pIVEX2.1 GFP plasmid containing a coding sequence for GFP and the control elements T7 promoter, ribosomal binding site and T7 terminator were tested in a purified and unpurified form in the in vitro expression.

Columns 2 and 4: 0.5 μg PCR product plus 5 μg unspecific sheared herring sperm DMA (HS DNA) columns 1 and 3: 1 μg PCR product.

EXAMPLE 1

Preparation of Template DNA

The plasmid pIVEX2.1 GFP which contained the sequence for the green fluorescent protein from Aequorea victoria in the form of a mutant GFPcycle 3 (Nature Biotechnology (1996) 14, 315–319) was cleaved for 2 h at 37° C. into 2830 bp, 1321 bp and 191 bp fragments on a preparative scale using 1.5 U SphI and EcoRV (Roche Diagnostics GmbH) per μg DNA. The 1321 bp fragment contained the coding sequence for GFP with the following important control elements for in vitro expression: T7 promoter, ribosomal binding site and T7 terminator.

A 1115 bp fragment was amplified with the Expand High Fidelity PCR kit (Roche Diagnostics GmbH) for in vitro expression starting with PCR fragments. The PCR product began 30 bp upstream of the T7 promoter and contained the GFP-coding sequence up to the end of the T7 terminator. The following primers were used for the amplification: sense primer 5' gcttagatcgagatctcgatcccgc-gaaattaatacgactcactataggagac cacaacggtttc and antisense primer 5' ggaagctttcagcaaaaaaccctcaagacccgtttagaggcccc aagg. 50 ng pIVEX2.1 GFP was used as the template. The PCR cycle of 1 min 94° C., 1 minute 65° C., 1 minute 72° C. was repeated 30 times. The concentration of the product was estimated by means of an agarose gel. The High Pure PCR Purification kit (Roche Diagnostics GmbH) was used to purify the PCR product.

Sheared herring sperm DNA and the circular plasmid pBR322 from Roche Diagnostics GmbH were used as unspecific competitor or sacrificial DNA.

EXAMPLE 2

Coupled In Vitro Transcription/Translation Reaction

Transcription/translation reactions were carried out in a volume of 50 μl for 2 hours at 30° C. The reaction solution contained 80.5 mM potassium acetate, 10 mM magnesium acetate, 35 mM ammonium chloride, 4 mM magnesium chloride, 4% polyethylene glycol 2000, 1 mM ATP, 0.5 mM CTP, 1 mM GTP, 0.5 mM UTP, 30 mM phosphoenolpyruvate, 8 μg/ml pyruvate kinase, 400 μM of each amino acid (all 20 naturally occurring amino acids), 0.1 mM folic acid, 0.1 mM EDTA, 50 mM HEPES-KOH pH 7.6/30° C., 20 μg/ml rifampicin, 0.03% sodium azide, 2 μg/ml aprotinin, 1 mg/ml leupeptin, 1 μg/ml pepstatin A, 10 mM acetylphosphate, 100 μg/ml tRNA from *E. coli* MRE600, 8 mM dithiothreitol, 100 U/ml Rnase-inhibitor, 15 μl *E. coli* lysate, 0.5 U/μl T7-RNA polymerase. The *E. coli* lysate was prepared from the A19 strain by the method of Zubay (Annu. Rev. Genet. (1973) 7, 267).

EXAMPLE 3

Figure 1:
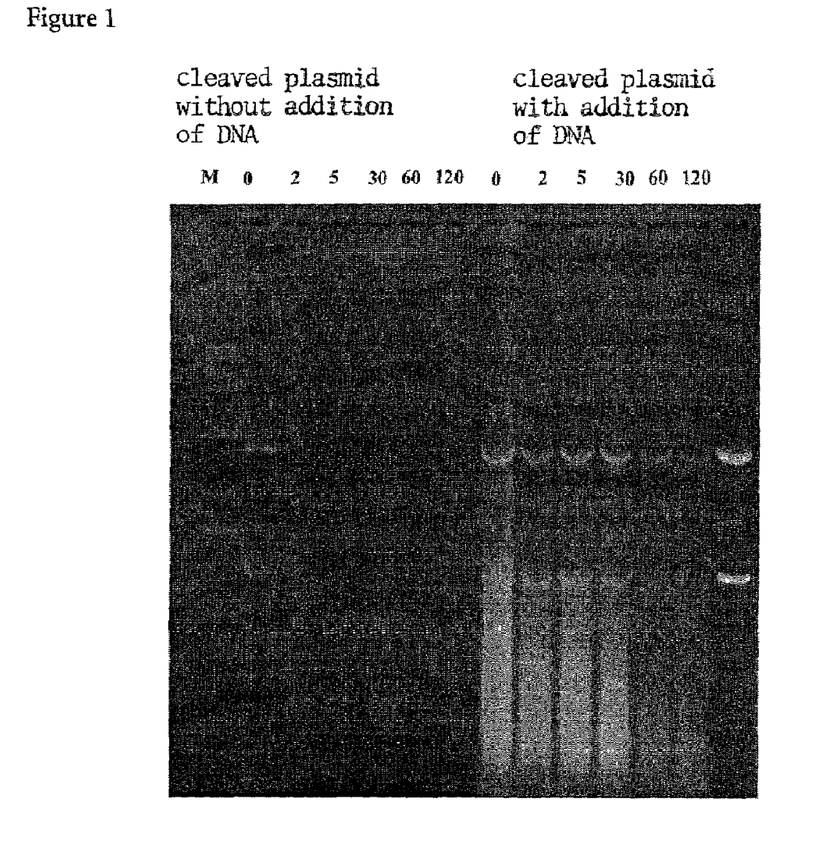
FIG. 1 shows the increased stability of linear DNA (plasmid fragments having a size of 2830 and 1321 base pairs) in a coupled transcription/translation mixture containing an *E. coli* S30 lysate in the presence of sheared herring sperm DNA lane 1:M=marker lanes 2–7: in vitro transcription/translation mixtures without DNA addition after 0, 2, 5, 30, 60 and 120 min incubation period.

FIG. 1:

Plasmid pIVEX2.1 GFP was cleaved on a preparative scale with 1.5 U each of SphI and EcoRV per μg DNA for 1 h at 37° C. into 2830 bp, 1321 bp and 191 bp fragments. 2 μg aliquots of the cleavage mixture were incubated for 0, 2, 5, 30, 60 and 120 minutes with 26 μg sheared herring sperm DNA in a 50 μl transcription/translation mixture. The same incubations were carried out without the addition of sheared unspecific DNA. After ethanol precipitation of the DNA, it was separated in a 1% agarose gel. (M, molecular weight marker; lane 14, cleaved plasmid without lysate addition).

EXAMPLE 4

Figure 2:
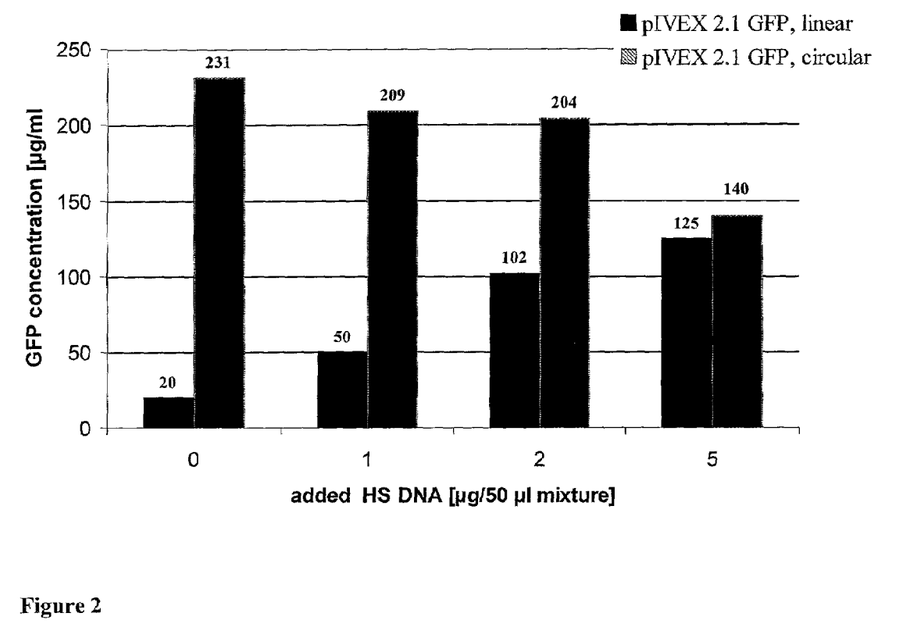
FIG. 2 shows an improvement of the protein synthesis rate specifically for linear template DNA by adding increasing amounts of sheared DNA.

FIG. 2:

EcoRV/Sph1-cleaved pIVEX2.1 GFP plasmid was incubated at 30° C. for 2 h in a coupled transcription/translation mixture containing *E. coli* S30 lysate. 0, 1, 2 and 5 μg unspecific sheared herring sperm DNA was added to the mixtures. The same incubations were carried out with uncleaved pIVEX2.1 GFP plasmid. GFP activity was measured by means of fluorescence spectroscopy. For the measurement the samples were diluted 1:50 to 1:400 depending on their content with 100 mM HEPES-KOH pH 7.6/30° C., 14 mM magnesium acetate, 60 mM potassium acetate, 0.5 mM dithiothreitol.

EXAMPLE 5

Figure 3:
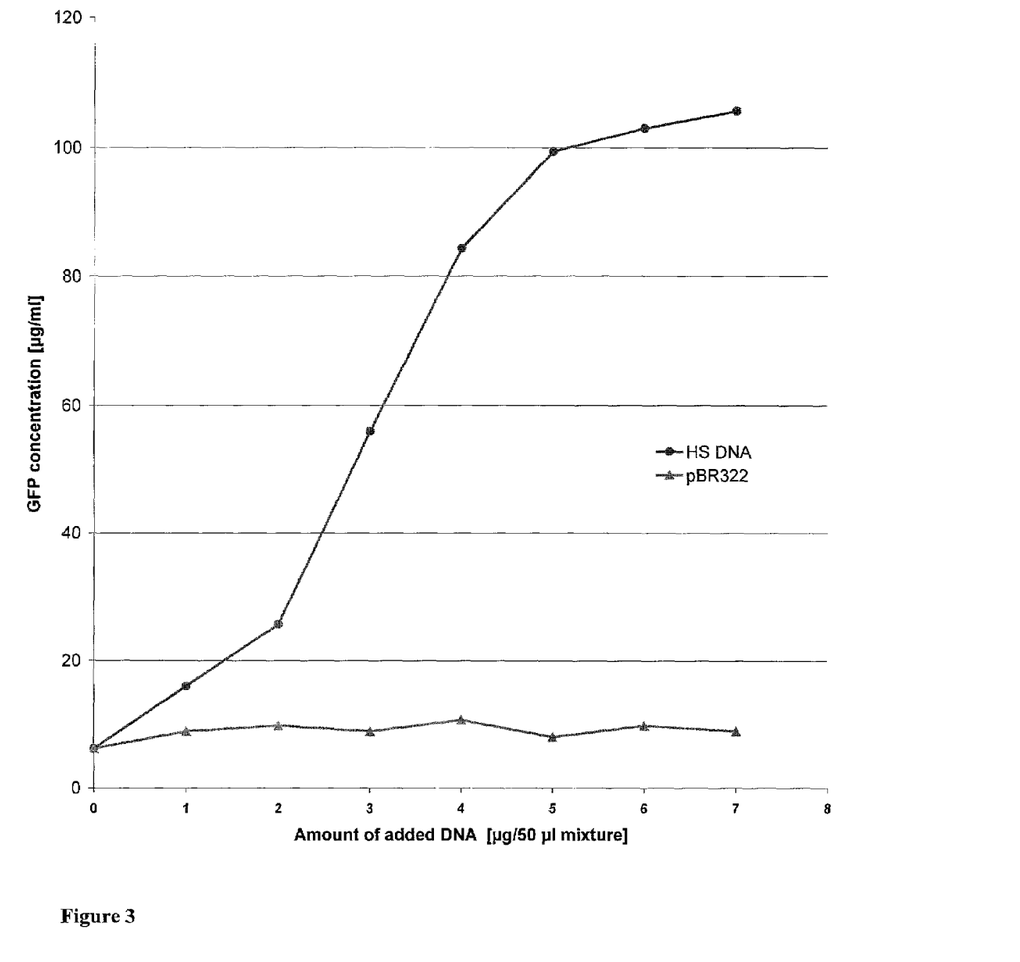
FIG. 3 shows that the addition of circular, unspecific DNA, in contrast to linear unspecific DNA, does not improve the rate of protein synthesis in a coupled transcription/translation mixture containing *E. coli* S30 lysate starting with a linear template.

FIG. 3:

EcoRV/Sph1-cleaved pIVEX2.1 GFP plasmid was incubated at 30° C. for 2 h in a coupled transcription/translation mixture containing *E. coli* S30 lysate. 0 to 7 μg unspecific sheared herring sperm DNA or 0 to 7 μg circular pBR322 plasmid was added to the mixtures. The GFP activity was measured by means of fluorescence spectroscopy as described in FIG. 2.

EXAMPLE 6

Figure 4:
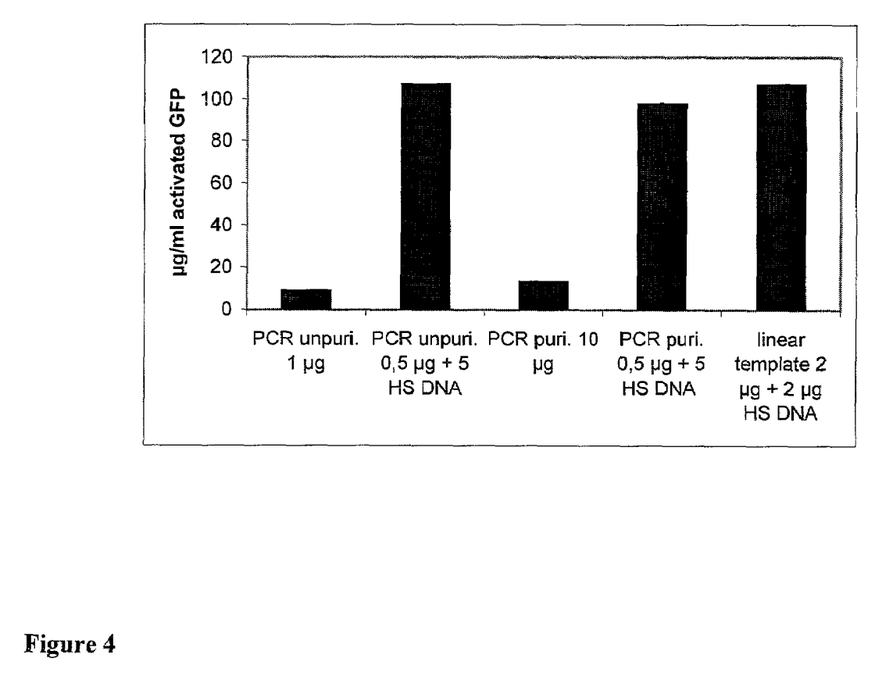
FIG. 4 shows an improved protein synthesis with addition of linear unspecific DNA in a coupled transcription/translation mixture containing an *E. coli* S30 lysate starting with an unpurified and purified PCR product.

FIG. 4:

The PCR product which contained the coding sequence for GFP and the control elements T7 promoter, ribosomal binding site and T7 terminator was tested in the in vitro expression in a purified and unpurified form. Mixtures containing 1 μg PCR product or 0.5 μg PCR product plus 5 μg unspecific sheared herring sperm DNA (HS DNA) were incubated for 2 h at 30° C. in a coupled transcription/translation mixture. The GFP activity was determined as described in FIG. 2 by means of fluorescence spectroscopy.

| | FIG. 1 | FIG. 2 | FIG. 3 | FIG. 4 |
|---|---|---|---|---|
| | cleaved plasmid without addition of DNA | | cleaved plasmid with addition of DNA | |
| GFP concentration [µg/ml] added HS DNA [µg/50 µl mixture] | | | linear | circular |
| GFP concentration [µg/ml] Amount of added DNA [µg/50 µl mixture] µg/ml activated GFP PCR unpuri. linear template 2 | PCR unpuri. | PCR unpuri. | PCR puri. | PCR puri. |

What is claimed is:

1. A method for in vitro protein synthesis in a coupled transcription/translation system, the method comprising:
   (a) preparing a reaction mixture comprising
      (i) a prokaryotic cellular lysate comprising one or more exonucleases,
      (ii) linear template DNA comprising a gene coding for the protein, wherein the template DNA comprises up to 10,000 base pairs,
      (iii) linear sacrificial DNA wherein the sacrificial DNA is not transcribed in the coupled system,
      (iv) nucleotides necessary for transcription of the template DNA into RNA, and
      (v) amino acids necessary for translation of the RNA into the protein, and
   (b) expressing and isolating the protein from the reaction mixture.

2. The method of claim 1, wherein the sacrificial DNA is selected from the group consisting of sheared DNA from herring sperm, salmon sperm, and calf thymus.

3. The method of claim 1, wherein the cellular lysate is an *E coli* lysate.

4. The method of claim 1, wherein the sacrificial DNA is present at a concentration of 1 to 200 µg/ml of the reaction mixture.

5. The method of claim 1, wherein the sacrificial DNA is present at a concentration of 10 to 100 µg/ml of the reaction mixture.

6. The method of claim 1, wherein the sacrificial DNA has a length of at least 10 base pairs.

* * * * *